United States Patent [19]

Borge et al.

[11] 4,002,554
[45] Jan. 11, 1977

[54] PROCESS OF MINIMIZING OR PREVENTING FOULING

[75] Inventors: Magne Borge, Rosieres; Torger Lode, Overijise, both of Belgium

[73] Assignee: Exxon Research & Engineering Co., Linden, N.J.

[22] Filed: Oct. 8, 1974

[21] Appl. No.: 513,078

[30] Foreign Application Priority Data

Oct. 17, 1973 United Kingdom ............ 48266/73

[52] U.S. Cl. .......................... 208/48 AA; 148/6.35; 165/133
[51] Int. Cl.$^2$ ......................................... C10G 9/16
[58] Field of Search ............... 134/2; 148/6.35; 21/2.5 R; 208/47, 48 R, 48 AA, 255; 203/9; 165/133

[56] References Cited

UNITED STATES PATENTS

| | | | |
|---|---|---|---|
| 1,582,407 | 4/1926 | King | 165/133 X |
| 2,245,561 | 6/1941 | Nelson et al. | 21/2.5 R |
| 2,388,041 | 10/1945 | Craig | 203/9 |
| 2,412,809 | 12/1946 | Harlow | 165/133 X |
| 2,557,684 | 6/1951 | Powers | 203/9 X |
| 3,308,056 | 3/1967 | Schultz | 208/128 |
| 3,309,412 | 3/1967 | Sakuragi et al. | 208/48 AA UX |
| 3,522,093 | 7/1970 | Woolman | 134/2 X |
| 3,848,017 | 11/1974 | Shalit | 208/128 X |

OTHER PUBLICATIONS

Schwabe, "Kinetics of Corrosion, Passivation and Inhibition of Ferrous Metals," Chemical Abstracts, vol. 73, 1970, No. 83055c.

Primary Examiner—Joseph Scovronek
Assistant Examiner—Arnold Turk
Attorney, Agent, or Firm—J. W. Ditsler; C. L. Kim

[57] ABSTRACT

Fouling is at least minimized when heating in a distillation unit a stream comprising $C_4$ or $C_5$ diolefins by a method wherein said distillation unit is flushed with an inert gas, thereafter nitric oxide is introduced in an amount ranging from 0.15 to 500, preferably from 5 to 30 gm of nitric oxide per square meter of internal surface area of said heating unit, the heating unit is thereafter flushed with inert gas and the $C_4$ or $C_5$ diolefin stream is introduced into the heating unit. This method may be applied to a depropanizer or a debutanizer the desorber and re-distillation of the CAA process for butadiene recovery, the extractive distillation, stripping tower and re-distillation of the ACN process for isoprene recovery, or extractive distillation, stripping tower and re-distillation of the ACN process for isoprene recovery.

6 Claims, No Drawings

PROCESS OF MINIMIZING OR PREVENTING FOULING

This invention relates to a process for minimising or preventing fouling when distilling streams containing $C_4$ and $C_5$ diolefins.

When distilling streams containing $C_4$ or $C_5$ diolefins derived from the steam cracking of petroleum feedstocks one often experiences the gradual build-up of rubber-like deposits on the interior of the distillation unit. This fouling often necessitates the shutdown of the distillation unit for cleaning. Sometimes fouling occurs rapidly within a few weeks, whereas in other cases it will take much longer. The fouling can be reduced to some extent by changing the operating conditions, e.g. reducing the temperature and pressure, but such changes are not sufficient to overcome the problem completely. It has been proposed to use certain additives which often act as dispersants; however they do not supress the fouling to any great extent.

According to our invention, fouling is minimized or prevented when heating in a heating unit a stream comprising $C_4$ or $C_5$ diolefins wherein said heating unit is flushed with an inert gas, thereafter nitric oxide is introduced in an amount ranging from 0.15 to 500 gm of nitric oxide per square meter of internal surface area of said heating unit, the heating unit is thereafter flushed with inert gas and the $C_4$ or $C_5$ diolefin stream is introduced into the heating unit.

The stream comprising $C_4$ or $C_5$ diolefins (or mixtures thereof) may be derived from any source but is usually derived directly or indirectly from the steam cracking of hydrocarbon feedstock. The hydrocarbon feedstock is preferably a petroleum hydrocarbon feedstock, and in particular a gas oil or naphtha. This feedstock is steam cracked i.e., thermally cracked in the presence of steam, at high temperature in a cracking unit. Usually this cracking unit is a tubular furnace and the cracking involves a short contact time and rather low pressure, e.g. 0.3 to 0.8 seconds and 1.5 to 3.5 atmospheres, respectively. Usually the cracking unit is a coil and the outlet temperatures of the coil may be maintained between 750° C and 850° C according to the feedstock used and the cracking severity required.

In the cracking of gas oil or naphtha the coil effluent is usually quenched rapidly, e.g. to about 300°–325° C, in the transfer line at the coil outlet to stop the cracking reaction and to minimise polymerization. Cracked effluent is further cooled in a quench tower or primary fractionator where the high boiling steam cracked gas oil and tar products are removed. In a typical design for the steam cracking of gas oil the lighter products overhead from the quench tower or primary fractionator are compressed to about 15 atmospheres and cooled to about 35°–40° C.

After recovery of $C_5$ plus material from compressor knockout drums and removal of acid gases, the gases are dried and typically introduced to a depropanizer tower. In this tower propane and lighter gases are taken overhead to become feed to the ethylene and propylene recovery facilities. Butane and heavier bottoms from the depropanizer flow to a debutanizer where the $C_4$ steam (almost entirely olefins and diolefins) is taken overhead and sent to butadiene and isobutylene recovery facilities.

Diolefins such as butadiene, isoprene and cyclopentadiene can be obtained from the steam cracking of naphthas and gas oils. The $C_4$ cut from the steam cracked product contains principally butene-1, butene-2, isobutene and butadiene-1,3. Butadiene can be recovered from the $C_4$ fraction by extraction (liquid-liquid separation) for example with cuprous ammonium acetate solution (CAA), or by extractive distillation (vapour-liquid separation) for example with aqueous acetonitrile (ACN).

In the CAA process the dienes and acetylenes form addition complexes with CAA and are separated from the butanes and butenes which have only limited physical solubility in CAA. The acetylenes which are most readily absorbed by CAA are generally removed in a prewash step. A series of refrigerated counterflow mixers and settlers are used in the main extraction train. For high butadiene recovery, lean solvent enters at the coldest stage where spent $C_4$ hydrocarbons are rejected, and flows countercurrent to the less soluble components. The bulk of the butadiene remaining in the rich solution is then desorbed by heating, scrubbed to recover ammonia evolved from the CAA and re-distilled to meet product specifications.

In the ACN process for butadiene ACN greatly increases the spread of relative volatilities so that reasonably sized distillation units can be used to separate butadiene from the other components in the $C_4$ fraction. The feed stream is carefully hydrogenated to reduce the acetylene level re-distillation, and then fed to a single stage extractive distillation unit. Feed enters near the middle of the extractive distillation tower, while lean aqueous ACN is added near but not at the top. Butenes and butanes go overhead an distillate with some being refluxed to the tower and the remainder are washed with water to remove entrained ACN. The tower bottoms i.e., ACN, butadiene with some butenes and acetylenes are fed to a recovery/stripping column. The hydrocarbons are taken overhead and then re-distilled to meet product specifications. The stripping column bottoms (ACN) are then returned near the top of the extractive distillation tower.

ACN can also be used for the recovery of isoprene from $C_5$ streams. The first step is the fractionation of steam cracker debutanizer bottoms in a conventional two-tower system to produce a $C_5$ cut containing about 30% isoprene. Two stages of extractive distillation with ACN are used where the ACN modifies the relative volatilities of the hydrocarbons. In the extractive distillation tower of each stage, the ACN solvent is introduced near the top and travels downward. Most of the impurities go overhead and the isoprene is carried down with the solvent. The overhead from this first stage comprises the bulk of the other $C_5$ hydrocarbons : pentenes and pentanes.

The tower bottoms from the first stage are fed to a recovery/stripping column and the stripping column bottoms are returned near the top of the distillation tower. Stripper overhead containing 80% isoprene and consisting almost entirely of dienes and acetylenes is fed to the second stage of extractive distillation. Isoprene goes overhead where it is water washed and re-distilled to 99.6 mole % purity.

The process of this invention is eminently suitable for use in the above-described processes, in particular in a depropanizer, a debutanizer, in the desorber and re-distillation of the CAA process for butadiene recovery, in the extractive distillation, stripping tower and re-distillation of the ACN process for butadiene recovery, or in the extractive distillation, stripping tower and re-distillation of the ACN process for isoprene recovery. Usually the $C_4$ or $C_5$ diolefin-containing stream is distilled in a distillation unit. However the process may be carried out in other heating units such as process vessels or piping.

Nitric oxide can be injected into the heating unit when it is temporarily out of use, i.e., the heating unit is passivated. Since nitric oxide will absorb much better on iron surfaces than on other metal surfaces, it is preferred that the walls of the heating unit be made of iron or steel, e.g. carbon steel.

To passivate the heating unit the unit is cleaned in the normal manner, dried, and thereafter flushed with the inert gas, e.g. nitrogen. Subsequently nitric oxide is added as rapidly as possible (e.g. a maximum of a few minutes) and in an amount ranging from 0.15 to 500, preferably from 5 to 30 gm of nitric oxide per square meter of internal surface area. Nitric oxide is rapidly absorbed into metal walls of the heating unit. This adsorption is virtually quantitative. Passivation is therefore accomplished after a few minutes but if desired the heating unit can be allowed to remain for days before removing the residual nitric oxide by flushing with an inert gas.

The unit is thereafter flushed with inert gas and it is then passivated and can thereafter be put on stream when desired.

Nitric oxide is effective in reducing both the amount and the molecular weight of the polymer formed as well as passivating the internal walls of the heating unit.

Nitric oxide is conveniently obtained from bottled gas via control valves.

EXAMPLE 1

A number of runs were carried out in a simulated reboiler. The reboiler was batch operated and contained a mixture of butadiene and solvent, in this case n-hexane. Evaporation took place in a heated tube, the vapours were condensed on top of a reservoir and liquid flowed from the bottom of the reservoir to the heating tube. The outside temperature of the heating tube was kept at 170° C and the temperature in the reservoir was kept at 90° C.

Fouling was observed when the heating tube became plugged by polymer formation causing an abrupt lowering of reservoir temperature.

The table lists the results obtained using the simulated reboiler. The first two runs were base case runs with well defined fouling at 23 and 27 hours. Most of the polymer recovered was solid polymer deposited on internal walls. The next 5 runs were carried out with base case plus various inhibitors, some of which increased run length before fouling. No appreciable reduction in polymer formation occurred in any of these cases, and the amount of soluble polymer remained low. The runs with NO passivation, however, showed a drastic reduction in polymer produced and in this case, most of the polymer was present in the liquid phase, i.e., it remained soluble and thus did not cause fouling. The last three runs were subsequent base case runs after NO runs 8 and 9. It is apparent that the passivation effect gradually disappeared.

TABLE

Effective of Additives on Reboiler Fouling

| Run | Charge | Run Length (hrs) | Fouled at (hrs) | Solid polymer (gms) | Soluble polymer (gms) | Total polymer Expected from theory (gms) |
|---|---|---|---|---|---|---|
|   |   | (2) |   |   | (3) | (4) |
| 1 | Base case(1) | 25 | 23 | 0.57 | 0.15 | 1.2 |
| 2 | Base case | 28 | 27 | 0.61 | 0.26 | 0.9 |
| 3 | B.C. + 500 ppm* 1 | 128 | 23 | 3.1 | 0.12 |   |
| 4 | B.C. + 500 ppm* 2 | 23 | 18 | 2.0 | 0.08 | 0.8 |
| 5 | B.C. + 500 ppm* 3 | 142 | 100 | 4.4 | 0.04 | 4.6 |
| 6 | B.C. + 500 ppm* 4 | 48 | 41 | 3.1 | 0.90 | 2.2 |
| 7 | B.C. + 50 ppm* 4 | 70 | 55 | 3.4 | 0.04 | 2.4 |
| 8 | B.C. + 15gm NO per m² internal surface area | 109 | No fouling | 0.3 | 0.8 | 3.5 |
| 9 | B.C. + 0.75 gm NO per m² internal surface area | 100 | No fouling | 0.8 | 4.5 |   |
| 10 | B.C. Passivated(5) | 74 | 69 | 0.63 | 1.24 | 4.2 |
| 11 | B.C. Passivated(6) | 116 | 92 | 0.91 | 1.5 | 4 |
| 12 | B.C. Passivated(6) | 108 | 98 | 2.7 | 0.09 | 4.5 |

(1)Butadiene: n-hexane = 3:2 by weight. Heating tube wall controlled at 170° C liquid reservoir at 90° C ~ 100 grams total charge (Base Case).
(2)Hours until heat was turned off.
(3)Determined as "Non Volatile Material"(NVM)
(4)Rate of thermally initiated, free radical polymerization of butadiene. Osugi, J & AL. The review of Physical Chemistry of Japan, Vol.35, No.2.1965.
(5)Apparatus was not opened at end of run No. 9, and run No. 10 was thus carried out on unopened equipment.
(6)Apparatus opened, cleaned and furnished with new heating tube for each of these runs.
*Commercially available additives.

The runs with NO listed in the Table showed that NO both reduced the amount of polymer formed and gave lower molecular weight polymer. It can be observed that the commercial anti-foulants in the Table, although they did not reduce the polymerization rate still managed to reduce the fouling. Their action is believed to be mainly that of a dispersant.

The last three runs in the Table showed that even after repeated cleanings of the laboratory reboilers, a strong inhibitory effect due to NO passivation was left. Iron and other metals form various compounds with NO, and these compounds are often reversible.

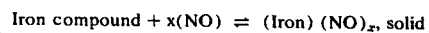
Iron compound + x(NO) ⇌ (Iron) (NO)$_x$, solid

Thus some NO will be formed in the heating zone after introduction of the hydrocarbon feedstock due to the above reaction. The last three runs in the Table clearly showed the effect of decreasing passivation.

EXAMPLE 2

A plant stream containing about 60 wt.% butadiene in addition to $C_2$-$C_5$ olefins was introduced in a reboiler at the conditions described in Example 1. Fouling occurred after 6 hours. The run was repeated adding 0.15 gm NO per m² of internal surface area to the dry test equipment for passivation. No fouling was observed after 100 hours operation.

EXAMPLE 3

In a plant depropanizer with two reboilers operating in parallel, two clean reboilers were started up. One was passivated by 10 g. NO/m² of internal surface area and the other was not passivated. After two months (the normal period for a production run) the non-passivated reboiler was covered with polymer and taken off for cleaning. After 5 months the passivated reboiler showed signs of polymer build-up. It was removed and inspected and found to contain less polymer than the non-passivated reboiler after two months.

EXAMPLE 4

In a typical plant ACN extractive distillation tower, the reboilers have to be changed and polymer removed every 44–50 days. One reboiler was passivated by 10 gm NO per square metre of internal surface are and ran for 150 days before cleaning was necessary.

What is claimed is:

1. A process for minimizing the fouling in the internal surface area of a metallic heating unit into which a hydrocarbon feedstock comprising a member selected from the group consisting of $C_4$ diolefins, $C_5$ diolefins or mixtures thereof is introduced, which comprises the steps of:
   1. purging said heating unit with an inert gas,
   2. introducing from 0.15 to 500 gm. of nitric oxide per square meter of the internal surface area into said heating unit purged in step (1),
   3. purging said heating unit passivated in step (2) with an inert gas, and, thereafter,
   4. introducing the hydrocarbon feedstock into said heating unit purged in step (3) with said heating unit being at an elevated temperature.

2. The process of claim 1 wherein from 5 to 30 gm. of nitric oxide per square meter of the internal surface area is introduced into said heating unit in step (2).

3. The process of claim 1 wherein the hydrocarbon feedstock is selected from the group consisting of naphtha, gas oil or mixtures thereof.

4. The process of claim 1 wherein the hydrocarbon feedstock is naphtha.

5. The process of claim 1 wherein the metallic heating unit comprises iron.

6. The process of claim 1 wherein the inert gas is nitrogen.

* * * * *